(12) United States Patent
Iwai et al.

(10) Patent No.: US 7,297,717 B2
(45) Date of Patent: Nov. 20, 2007

(54) EMULSION COSMETIC

(75) Inventors: Hidetaka Iwai, Tokyo (JP); Tomohiko Sano, Tokyo (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 09/842,161

(22) Filed: Apr. 26, 2001

(65) Prior Publication Data

US 2001/0053376 A1 Dec. 20, 2001

(30) Foreign Application Priority Data

Apr. 27, 2000 (JP) .............................. 2000-128176
Sep. 13, 2000 (JP) .............................. 2000-277471

(51) Int. Cl.
*A61K 8/06* (2006.01)

(52) U.S. Cl. ..................... 514/937; 514/938; 424/401

(58) Field of Classification Search ............... 424/401, 424/70.1, 70.11, 70.21, 70.23, 70.24, 70.27, 424/70.31, 73; 514/937, 938
See application file for complete search history.

(56) References Cited

U.S. PATENT DOCUMENTS

| | | | | |
|---|---|---|---|---|
| 4,908,154 A | * | 3/1990 | Cook et al. ............... | 252/314 |
| 5,562,911 A | * | 10/1996 | Brunetta et al. ............ | 424/401 |
| 5,876,702 A | * | 3/1999 | Gers-Barlag et al. ........ | 424/59 |
| 6,066,316 A | * | 5/2000 | Shiojima et al. | |
| 6,121,228 A | * | 9/2000 | Drapier et al. .............. | 510/417 |
| 6,468,551 B1 | * | 10/2002 | Diec et al. .................. | 424/401 |

FOREIGN PATENT DOCUMENTS

| | | |
|---|---|---|
| EP | 0 579 455 | 1/1994 |
| JP | 63-126542 | 5/1988 |
| JP | 63-126543 | 5/1988 |
| JP | 1-293131 | 11/1989 |
| JP | 2-78432 | 3/1990 |
| JP | 4-48925 | 2/1992 |

OTHER PUBLICATIONS

Ansel, Pharmaceutical Dosage Forms and Drug Delivery Systems, 1990, pp. 240-249.*
Flick, E., Cosmetic Additves, 1991, Noyes Publications, p. 777.*
Database WPI, Week 198827, Derwent Publications Ltd., London, GB; AN 1988-187880 '271 XP002257177 (Based on JP 63 126542, May 30, 1988).
Database WPI, Week 198827, Derwent Publications Ltd., London, GB; AN 1988-187881 '251 XP002257178 (Based on JP 63 126543, May 30, 1988).

* cited by examiner

*Primary Examiner*—Sreeni Padmanabhan
*Assistant Examiner*—Gina C. Yu
(74) *Attorney, Agent, or Firm*—Oblon, Spivak, McClelland, Maier & Neustadt, P.C.

(57) ABSTRACT

An oil-in-water type emulsion cosmetic which contains (A) a hydrophilic surface active agent, (B) an oily component and (C) water, and weight ratio of the component (B) is 10 or more based on 1 of the component (A).

18 Claims, No Drawings

EMULSION COSMETIC

FIELD OF THE INVENTION

This invention relates to an oil-in-water type emulsion cosmetic which can include a large amount of oily components, has high transparency and gives an emulsion system stable within a broad temperature range.

BACKGROUND OF THE INVENTION

In order to include an oily component transparently in an emulsion cosmetics, there is a method in which the oily component is solubilized in micelles formed by a surface active agent. However, since the amount of the oily component to be solubilized is extremely small, its effects in sufficiently exerting functions of the oily component and improving touch to the skin are not satisfactory.

Also known are micro-emulsion methods which use surface chemical properties of surface active agents, such as liquid crystal emulsification, D-phase emulsification and phase inversion emulsification, but these methods also have a limitation regarding the amount of oily component which can be involved transparently (JP-A-63-126542; the term "JP-A" as used herein means an "unexamined published Japanese patent application"). They also have other limitations, e.g. the kinds of surface active agents are limited because the surface chemical properties thereof are spoiled in some cases depending on the kinds of an oily component to be jointly used.

On the other hand, a high pressure emulsification method is known in which a refined emulsion having an average emulsion particle size of 0.2 µm or less is obtained by making use of a high pressure emulsifier (e.g., JP-A-63-126543, JP-A-4-48925).

The refined emulsion obtained by high pressure emulsification method generally has a low viscosity of between 10 and 100 mPa·s, so that its use is limited. Though a gelatinous emulsion which has relatively high viscosity can be applied to various cosmetics such as moisturizing lotion, body lotion and hair treatment, the refined emulsion cannot be used as such due to its low viscosity, so that there is a method to increase the viscosity using a water-soluble thickener. However, a product thickened with a thickener frequently becomes sticky just as it dries after its application, so that there is a great demand for an emulsion cosmetic which is transparent and high in viscosity and has good feeling in use.

SUMMARY OF THE INVENTION

The object of the invention is to provide an oil-in-water type emulsion cosmetic which can include stably with a large amount of oily components within a broad temperature range, can efficiently exert effects of the touch such as moist feel and oiliness and of the oily components and also has high transparency.

The present inventors have found that an emulsion cosmetic in which a large amount of oily component is dispersed stably within a broad temperature range can be obtained by emulsifying a hydrophilic surface active agent, an oily component and water using an emulsifier having strong shearing force.

The inventors have found also that the emulsion cosmetic which also has a characteristic of high viscosity can be obtained by emulsifying an oily component containing solid fatty material and water together with a hydrophilic surface active agent using an emulsifier having strong shearing force.

The invention is to provide an oil-in-water type emulsion cosmetic which comprises (A) a hydrophilic surface active agent, (B) an oily component and (C) water, wherein weight ratio of the component (B) is 10 or more based on 1 of the component (A).

DETAILED DESCRIPTION OF THE INVENTION

The surface active agent to be used in the invention is a hydrophilic surface active agent selected from an anionic surface active agent, a cationic surface active agent, an amphoteric surface active agent and a nonionic surface active agent having an HLB value of 9 or more, and preferred among them is an agent containing an alkyl or alkenyl group having from 10 to 24, preferably from 12 to 18, of carbon atoms, as a hydrophobic group. According to the invention, the term "hydrophilic surface active agent" means an surface active agent which can produce an oil-in-water type (O/W) emulsion.

Examples of the anionic surface active agent include a higher fatty acid salt such as sodium laurate or potassium palmitate, an alkyl sulfate ester salt such as sodium lauryl sulfate or potassium lauryl sulfate, an alkyl ether sulfate ester salt such as polyoxyethylene (to be referred to as POE herein after) lauryl sulfate triethanolamine, an N-acylsarcosinic acid such as sodium lauroylsarcosine, a higher fatty acid amide sulfonic acid salt such as sodium N-myristoyl-N-methyltaurine, a phosphoric acid ester salt such as POE oleyl ether sodium phosphate or POE stearyl ether sodium phosphate, a sulfosuccinic acid salt such as sodium di-2-ethylhexylsulfosuccinate, an alkylbenzenesulfonic acid salt such as sodium linear dodecylbenzenesulfonate or linear dodecylbenzenesulfonic acid triethanolamine, and an N-acylglutamic acid salt such as monosodium N-lauroylglutamate, disodium N-stearoylglutamate or monosodium N-myristoyl-L-glutamate.

Examples of the cationic surface active agent include an alkyltrimethylammonium salt such as stearyltrimethylammonium chloride or lauryltrimethylammonium chloride, and a dialkyldimethylammonium salt, a trialkylmethylammonium salt and an alkylamine salt.

Examples of the amphoteric surface active agent include an imidazoline amphoteric surface active agent such as 2-undecyl-N,N-(hydroxyethylcarboxymethyl)-2-imidazoline sodium salt or 2-cocoyl-2-imidazoliniumhydroxide-1-carboxyethyloxy disodium salt, a betaine amphoteric surface active agent such as 2-heptadecyl-N-carboxymethyl-N-hydroxyethylimidazoliniumbetaine, lauryldimethylaminoacetic acid betaine, alkylbetaine, amidobetaine or sulfobetaine, and an amino acid type amphoteric surface active agent such as N-laurylglycine, N-lauryl-β-alanine or N-stearyl-β-alanine.

The nonionic surface active agent preferably has an HLB value of 9 or more, more preferably from 10 to 17, most preferably from 12 to 17, in order to provide a stable emulsion system. The term HLB means an index which shows hydrophilic-lipophilic balance and is defined by the following formula of Oda, Teramura et al.

$$HLB = \frac{\sum \text{inorganic value}}{\sum \text{organic value}} \times 10$$

Examples of such a nonionic surface active agent include a polyoxyethylene alkyl ether, a polyoxyethylene alkenyl ether, a polyoxyethylene alkylphenyl ether, a polyoxyethylene hydrogenated castor oil, a polyoxyethylene glycerol fatty acid ester, a polyoxyethylene sorbitan fatty acid ester, a polyoxyethylene sorbitol fatty acid ester, a higher fatty acid sucrose ester, a polyglycerol fatty acid ester, a polyglycerol alkyl ether and an alkylglucoside surface active agent.

Preferred among these hydrophilic surface active agents are N-stearoylarginine monosodium salt, N-stearoyl-L-glutamic acid monosodium salt, N-myristoyl-N-methyltaurine sodium salt, N-stearoyl-N-methyltaurine sodium salt, oleic acid triethanolamine salt, polyoxyethylene(4) lauryl ether phosphate sodium salt, polyoxyethylene(6) tridecyl ether acetate sodium salt, polyoxyethylene(30) cetyl ether, stearyltrimethylammonium chloride and cetyltrimethylammonium bromide.

These hydrophilic surface active agents may be used as a mixture of two or more. Also, it is desirable that the surface active agent has a dynamic surface tension of 57 mN/m or less, particularly 55 mN/m or less, measured at 25° C. for 100 msec (by an automatic dynamic surface tension meter BP-D3, mfd. by Kyowa Surface Science), which is evaluated by the bubble pressure method.

It is desirable that the oil-in-water type cosmetic of the invention contains from 0.01 to 8% by weight (sometimes to be referred simply to as % hereinafter), preferably from 0.1 to 6% by weight, of the hydrophilic surface active agent.

The oily component of the oil-in-water type cosmetic of the invention may be a liquid oily component alone, but preferably comprises a liquid oily component and a solid fatty material. The liquid oily component is a component which is liquid at ordinary temperature, generates two phase separation when mixed with water of 20° C. and exerts certain effects such as the addition of flexibility and lubricity to the skin and hair and the inhibition of penetration of substances such as a stimulant from the outside and transpiration of moisture from the inside by forming a film.

Examples of the liquid oily component include hydrocarbon oils such as liquid paraffin, squalane, n-octane, n-heptane and cyclohexane; ether oils such as dioctyl ether, ethylene glycol monolauryl ether, ethylene glycol dioctyl ether and glycerol monooleyl ether; ester oils such as octyldodecyl myristate, isopropyl palmitate, butyl stearate, myristyl myristate, isopropyl myristate, di-2-ethylhexyl adipate, diisopropyl sebacate, neopentyl glycol dicaprate and tricaproin; saturated higher alcohols such as isostearyl alcohol and octyldodecanol; unsaturated higher alcohols such as oleyl alcohol and lanolin alcohol; higher fatty acids such as eicosenoic acid, isomyristic acid and capric acid; higher fatty acid amides such as lauroyl laurylamine and lauric acid butylamide; oils and fats such as olive oil, soybean oil and cotton seed oil; silicone oils such as dimethylpolysiloxane, cyclic dimethylpolysiloxane, methylphenylpolysiloxane, amino-modified silicone, epoxy-modified silicone, carboxy-modified silicone, alcohol-modified silicone, alkyl-modified silicone, polyether-modified silicone and fluorine-modified silicone; and fluorine based oils such as perfluoroalkylethyl phosphate, perfluoroalkylpolyoxyethylene phosphate, perfluoro polyether and polytetrafluoroethylene.

Particularly preferred are liquid paraffin, squalane, neopentyl glycol dicaprate, ethylene glycol monolauryl ether, perfluoro polyether and dimethyl polysiloxane. These oily components may be used as a mixture of two or more. Also, it is desirable that these oily components have a surface tension of 29 mN/m or less, particularly 28 mN/m or less, at 25° C. (measured using CBVP-A3 mfd. by Kyowa Surface Science).

It is desirable that the oil-in-water type cosmetic of the invention contains from 0.1 to 80% by weight, particularly from 1 to 70% by weight, of the liquid oily component.

Next, the solid fatty material is an oily substance which is solid at 25° C., preferably an aliphatic compound selected from an aliphatic alcohol, cholesterol, a fatty acid, an aliphatic amide derivative and an aliphatic amine derivative. Among these compounds, preferred examples of the aliphatic alcohol include saturated aliphatic alcohols having from 12 to 24 carbon atoms, such as lauryl alcohol, myristyl alcohol, cetanol, stearyl alcohol andbehenyl alcohol. Also, preferred examples of the fatty acid include saturated fatty acids having from 12 to 24 carbon atoms, such as lauric acid, myristic acid, palmitic acid, stearic acid and behenic acid. Preferred examples of the aliphatic amide derivative include ceramides and analogous substances thereof; such as type I to type VI natural ceramides, N-(2-hydroxy-3-hexadecyloxypropyl)-N-2-hydroxyethylhexadecanamide and N-(2-hydroxy-3-hexadecyloxypropyl)-N-2-hydroxyethyldecanamide. Preferred examples of the aliphatic amine derivative include sphingosines such as sphingosine, dihydrosphingosine, phytosphingosine, dehydrosphingosine, dehydrophytosphingosine, sphingadienine and N-methyl or N,N-dimethyl compounds thereof, and 1-(2-hydroxyethylamino)-3-isostearyloxy-2-propanol. Among these compounds, cetanol, stearyl alcohol, cholesterol, stearic acid, palmitic acid, ceramides and analogous substances thereof and sphingosines are particularly desirable.

It is desirable that the solid fatty material is used within the range of from 0.01 to 0.5 part by weight based on 1 part by weight of the liquid oily component and contained in the oil-in-water type cosmetic of the invention in an amount of from 1 to 30% by weight, particularly from 2 to 20% by weight.

The oil-in-water type cosmetic of the invention is produced by emulsifying a hydrophilic surface active agent, an oily component and a water phase with high shearing force. In this case, it is desirable that weight ratio of (A) a hydrophilic surface active agent and (B) an oily component is 10 or more of the component (B) based on 1 of the component (A), preferably from 10 to 38 of the component (B) based on 1 of the component (A). In this connection, when two or more hydrophilic surface active agents and oily components are used, the ratio is calculated by respective total amounts.

It is desirable that the oil-in-water type cosmetic of the invention contains from 5 to 99.85% by weight, particularly from 10 to 98.9%, of the water phase, and from 1 to 99.85%, particularly from 2 to 98% by weight, of water.

It is desirable that the water phase has a surface tension of 58 mN/m or less, particularly 57 mN/m or less, at 25° C. (measured using a full automatic surface tension meter CBVP-Z mfd. by Kyowa Surface Science).

In order to reduce surface tension of the water phase, the emulsion cosmetic of the invention may include water-soluble alcohols. Examples of the water-soluble alcohols include methyl alcohol, ethyl alcohol, propyl alcohol, isopropyl alcohol, ethylene glycol, propylene glycol, 1,3-butylene glycol, glycerol, sorbitol, mannitol, diethylene glycol, dipropylene glycol, polyethylene glycol (molecular weight, 400 to 20,000), sorbitan, sorbitol, maltose, maltotriose and sodium hyaluronate.

It is desirable that the emulsion cosmetic of the invention contains these alcohols in an amount of from 0.2 to 66% by weight, preferably from 1 to 33% by weight.

It is desirable that the emulsification with a high shearing force is carried out using an emulsifier which can provide a maximum shearing force of 10,000 s$^{-1}$ or more, particularly a shearing force of from 10,000 to 100,000,000 s$^{-1}$.

Such a high shearing force can be obtained by a commercial high pressure emulsifier such as Filmix (mfd. by Tokushu Kika), Creamix (mfd. by M Technique), Microfluidizer (mfd. by Microfluidics) or DeBEE 2000 (mfd. by B.E.E. International). For example, a micro-emulsion of interest can be obtained by setting the injection pressure to 300 to 3,000 kg/cm$^2$ and the temperature to 5 to 50° C. However, these operation conditions such as injection pressure and temperature are not particularly limited, because they vary depending on the technical specification of each apparatus.

Alternatively, a desired emulsion can also be obtained more efficiently, by applying the same high shearing force treatment to a preliminary emulsion obtained by a usual emulsification method. As occasion demands, this high shearing force treatment may be carried out repeatedly.

The oil-in-water type emulsion cosmetic obtained in this manner contains the oily component in a large amount and forms stable micro-emulsion. Average particle size of the emulsion particles is, for example, from 0.01 to 1.0 μm, and more preferably, an emulsion having high transparency can be obtained within the range of from 0.01 to 0.2 μm. The average particle size is measured by a laser diffraction/scattering method. Also, transparency of the emulsion can be evaluated by an ultraviolet and visible region absorption photometer and judged transparent when the light transmittance at a wavelength of 550 nm is 50% or more.

When a liquid oily component is used alone as the oily component, the resulting emulsion has a relatively low viscosity, but an emulsion having high viscosity can be obtained by the use of a solid fatty material in addition to the liquid oily component as the oily component. In this case, an emulsion having a viscosity within a range, for example from 200 to 1,000,000 mPa·s at 25° C., can be obtained by adjusting the solid fatty material.

According to the oil-in-water type emulsion cosmetic of the invention, stable dispersion can be effected in an emulsion having good transparency, by also including a solid fatty material in microscopic oil droplets in this manner.

In addition, when the oil-in-water type emulsion cosmetic is applied to the skin, it exerts an effect to improve percutaneous absorption of the solid fatty material component in comparison with generally known cosmetics including similar solid fatty material.

Also, an emulsion in which its oil phase content and viscosity are adjusted can be obtained by firstly producing an oil-in-water type emulsion having high oil phase content, also preferably having high viscosity, and then further diluting it with water or an aqueous medium.

The term "aqueous medium" as used herein means a mixture of water and water-soluble alcohols, and examples of the water-soluble alcohols include methanol, ethanol, propanol, isopropanol, ethylene glycol, propylene glycol, 1,3-butylene glycol, glycerol, sorbitol, mannitol, diethylene glycol, dipropylene glycol, polyethylene glycol (molecular weight, 400 to 20,000), sorbitan, sorbitol, maltose, maltotriose and sodium hyaluronate.

In this case, viscosity can also be adjusted by adding a water-soluble high polymer. Adjustment of a predetermined viscosity can be effected by its kind, mixing amount and neutralizing degree.

Examples of the water-soluble synthetic high polymer include a polyvinyl alcohol, a sodium polyacrylate, a carboxyvinyl polymer, a polyacrylamide, a polyvinyl pyrrolidone, a polyvinyl methyl ether, a polyvinyl sulfone, a maleic acid copolymer, a polyethylene oxide, a polydiaryl amine, a polyethylene imine, a water-soluble cellulose derivative (e.g., carboxymethyl cellulose, methyl cellulose, methylhydroxypropyl cellulose, hydroxyethyl cellulose, hydroxypropyl cellulose or cellulose sulfate sodium salt) and a starch derivative (e.g., oxidized starch, dialdehyde starch, dextrin, British gum, acetyl starch, starch phosphate, carboxymethyl starch, hydroxyethyl starch or hydroxypropyl starch).

Examples of the water-soluble natural high polymer include gum arabic, tragacanth gum, karaya gum, guar gum, tara gum, locust bean gum, tamarind gum, sodium alginate, alginic acid propylene glycol ester, carrageenan, pharcellulan, agar, high methoxy pectin, low methoxy pectin, chitin, chitosan, starches (e.g., starch derived from corn, potato, wheat, rice, sweet potato or tapioca, α-starch and soluble starch), fermentation polysaccharides (e.g., xanthan gum, pullulan, curdlan and dextran), proteins (e.g., casein sodium, gelatin and albumin), chondroitin sulfate and hyaluronic acid.

Preferred among these water-soluble high polymers are polyethylene oxide (molecular weight, 100,000 to 5,000,000), polyvinyl alcohol, sodium polyacrylate, carboxyvinyl polymer, water-soluble cellulose and carrageenan.

These water-soluble high polymers can form aqueous gel, for example, by adding to and dissolving in a stirred water phase heated at 60° C., spontaneously cooling to about room temperature and then adding a neutralizing agent as occasion demands. The content in the oil-in-water type emulsion cosmetic of the invention is generally from 0.01 to 30% by weight, but since it varies depending on the kind and neutralization degree of each water-soluble high polymer, it is optionally selected in such an amount that viscosity of the formulated product is adjusted to a value within the range described above.

In addition to the above, water-soluble or oil-soluble components such as a chelating agent, a pH adjusting agent, an antiseptic, a thickener, a drug component and a plant component can be formulated optionally.

The emulsion cosmetic of the invention can be used as hair cosmetics such as hair liquid, hair mousse, shampoo and rinse; shaving cosmetics such as after-shaving lotion; skin cosmetics such as body lotion, face lotion, toilet lotion, moisturizing lotion and bath liquid, and body shampoo. The components to be optionally formulated depending on each purpose may be formulated after obtaining the micro-emulsion or contained in advance before the high speed shearing treatment.

EXAMPLES

Inventive Examples 1 to 6 and Comparative Examples 1 to 3

The components shown in Table 1 excluding water and ethanol were mixed in advance with heating at 80° C., and the thus dissolved phase was mixed with water of 80° C. to carry out preliminary emulsification under propeller stirring. After cooling to 25° C., ethanol was added (if necessary) and an emulsion cosmetic was produced using a high pressure emulsifier (DeBEE 2000, mfd. by B.E.E. International), by passing through the solution 10 times at a shear rate of 1,000,000 s$^{-1}$. In the Comparative Examples, each cosmetic was produced by cooling the preliminary emulsion to room temperature and then passing through the emulsion 10 times at a shear rate of 5,000 s$^{-1}$ using the same high pressure emulsifier.

The appearance, average particle size and periodical stability of the thus produced emulsion cosmetics are shown in Table 1.

In this connection, the appearance was evaluated by measuring light transmittance at a wavelength of 550 nm in a 1 cm cell using an ultraviolet and visible region absorption photometer (UV-160, mfd. by Shimadzu). A light transmittance of 50% or more was judged transparent. The average particle size was measured by a laser diffraction/scattering type particle size distribution measuring machine (HORIBA-500, mfd. by Horiba). Regarding the periodical stability, changes after one month of storage at a temperature of −5° C., 25° C. or 40° C. were observed.

TABLE 1

|  | Inventive Example | | | | | | Comparative Ex. | | |
| --- | --- | --- | --- | --- | --- | --- | --- | --- | --- |
|  | 1 | 2 | 3 | 4 | 5 | 6 | 1 | 2 | 3 |
| N-Stearoylarginine monosodium | 0.5 | 1.0 |  |  |  |  | 0.5 | 0.4 |  |
| N-Myristoyl-N-methyltaurine sodium |  |  | 0.5 | 0.5 | 1.0 |  |  | 0.5 | 0.5 |
| Stearyltrimethylammonium chloride |  |  |  |  |  | 0.5 |  |  |  |
| Cetanol | 0.67 | 0.36 | 0.30 | 0.36 | 0.67 | 0.67 | 0.67 | 0.50 | 0.30 |
| Stearyl alcohol | 0.53 | 0.24 | 0.20 | 0.24 | 0.53 | 0.53 | 0.53 | 0.40 | 0.20 |
| Dimethyl polysiloxane (6 mm$^2$/s) | 5.1 | 10.0 |  |  | 4.0 |  | 5.1 | 4.0 |  |
| Squalane |  |  | 5.0 |  | 6.0 |  |  | 6.0 | 5.0 |
| Isopropyl myristate |  |  |  | 5.0 |  | 5.0 |  |  |  |
| Glycerol | 3.6 | 10.0 | 4.2 | 4.2 | 4.2 | 6.0 | 3.6 | 10.0 | 4.2 |
| Dipropylene glycol | 2.0 | 2.0 |  | 2.0 | 2.0 | 3.0 | 2.0 | 2.0 |  |
| Purified water | 82.6 | 74 | 89.8 | 87.7 | 72.9 | 84.3 | 82.6 | 74 | 89.8 |
| Ethanol | 5.0 | 2.4 |  |  | 8.7 |  | 5.0 | 2.4 |  |
| Appearance |  |  | transparent |  |  |  |  | cloudy |  |
| Average particle size (μm) | 0.09 | 0.12 | 0.07 | 0.08 | 0.13 | 0.06 | 0.35 | 1.50 | 0.60 |
| Light transmittance |  |  |  |  |  |  |  |  |  |
| (Just after production) | 87.8 | 83.2 | 92.2 | 88.0 | 80.7 | 90.1 | 32.2 | 10.3 | 19.3 |
| (After 1 month at −5° C.) | 87.2 | 81.2 | 91.7 | 85.4 | 77.7 | 86.3 | * | * | * |
| (After 1 month at 25° C.) | 87.5 | 84.8 | 90.7 | 88.1 | 78.1 | 89.1 | * | * | * |
| (After 1 month at 40° C.) | 83.3 | 80.7 | 89.9 | 83.1 | 76.7 | 88.0 | * | * | * |

* Two phase separation

TABLE 2

|  | Inventive Example | | | |
| --- | --- | --- | --- | --- |
|  | 7 | 8 | 9 | 10 |
| N-Stearoylarginine monosodium | 0.3 |  |  |  |
| N-Myristoyl-N-methyltaurine sodium |  | 0.5 | 0.5 |  |
| Stearyltrimethylammonium chloride |  |  |  | 0.5 |
| Cetanol | 0.18 | 0.30 | 0.12 | 0.12 |
| Stearyl alcohol | 0.12 | 0.20 | 0.08 | 0.08 |
| Dimethyl polysiloxane (6 mm$^2$/s) | 3.0 | 5.0 |  |  |
| Squalane |  |  | 5.0 |  |
| Isopropyl myristate |  |  |  | 5.0 |
| Glycerol | 2.5 | 4.0 | 4.2 | 3.0 |
| Dipropylene glycol | 2.0 | 1.5 |  |  |
| Purified water | 88.9 | 86.1 | 90.1 | 89.3 |
| Ethanol | 3.0 | 2.4 |  |  |
| Average particle size (μm) | 0.09 | 0.12 | 0.07 | 0.08 |
| Light transmittance (%) (just after production) | 92.6 | 90.5 | 79.2 | 75.3 |

As shown in Table 1, all of Inventive Examples 1 to 6 of the invention provided emulsions having high transparency, and their appearance was stably maintained after one month of storage at each temperature.

Inventive Examples 7 to 10

Emulsion cosmetics were produced based on the formulations shown in Table 2 in the same manner as described in Inventive Example 1. All of the products showed high transparency, and their appearance was stable for 6 months or more at −5° C., 25° C. and 40° C.

Inventive Examples 11 to 14

Among the composition shown in Table 3, components other than water and ethanol were mixed and heated at 80° C., and the thus dissolved phase was mixed with water heated in advance at 80° C. to carry out preliminary emulsification under propeller stirring. After spontaneous cooling to 25° C., ethanol was added and respective emulsion cosmetics were produced using Microfluidizer M-140K (mfd. by Microfluidics), by passing through the solution 3 times at a shear rate of 1,000,000 s$^{-1}$. As shown in Table 3, all of the emulsion cosmetics of Inventive Examples 11 to 14 showed high transparency and excellent periodical stability.

TABLE 3

|  | Inventive Example | | | |
|---|---|---|---|---|
|  | 11 | 12 | 13 | 14 |
| N-Stearoylarginine monosodium | 1.2 | 2.0 | — | 1.6 |
| Polyoxyethylene (30) cetyl ether | — | — | 1.6 | — |
| Glycerol | 14.1 | 12.3 | 14.1 | 14.1 |
| 1,3-Butanediol | — | 5.0 | — | — |
| Ceramides analogue* | 5.0 | 6.0 | 5.0 | 5.0 |
| Dimethyl polysiloxane (6 mm$^2$/s) | 19.2 | 20.4 | 16.0 | — |
| Perfluoro polyether** | — | — | — | 16.0 |
| Purified water | 52.8 | 46.5 | 49.3 | 50.3 |
| Ethanol | 7.7 | 7.7 | 14.0 | 13.0 |
| Appearance | transparent | | | |
| Average particle size (μm) | 0.09 | 0.08 | 0.09 | 0.07 |
| Light transmittance (%) | | | | |
| (Just after production) | 80.2 | 85.7 | 78.3 | 84.2 |
| (After 1 month at −5° C.) | 77.2 | 81.4 | 74.7 | 76.3 |
| (After 1 month at 25° C.) | 77.0 | 85.4 | 78.7 | 89.1 |
| (After 1 month at 40° C.) | 76.3 | 84.7 | 80.7 | 88.0 |

*Ceramides analogue; N-(2-hydroxy-3-hexadecyloxypropyl)-N-2-hydroxyethylhexadecanamide
**FOMBLIN HC/04 (mfd. by Ausimont)

| Cleansing preparation (%) | |
|---|---|
| Liquid paraffin | 40.0 |
| Perfume | adequate amount |
| Antiseptic | adequate amount |
| Oleic acid triethanolamine salt | 3.8 |
| Glycerol | 5.0 |
| Water | 50.2 |

| Moisturizing lotion (%) | |
|---|---|
| Dimethyl polysiloxane (5 mm$^2$/s) | 10.0 |
| Perfume | adequate amount |
| Antiseptic | adequate amount |
| N-Myristoyl-N-methyltaurine sodium | 1.0 |
| Cetanol | 0.6 |
| Glycerol | 12.0 |
| Water | 76.4 |

| Hair rinse (%) | |
|---|---|
| High polymer dimethylsilicone (10 mm$^2$/s) | 40.0 |
| Perfume | adequate amount |
| Antiseptic | adequate amount |
| Cetyltrimethylammonium bromide | 3.5 |
| Water | 38.5 |
| Glycerol | 28.0 |

All of the cosmetics of Inventive Examples 15 to 17 showed high transparency and were stable for 6 months or more at room temperature.

Inventive Example 18 and Comparative Examples 4 and 5

In Inventive Example 18, the components shown in Table 4 excluding water and ethanol were mixed in advance with heating at 80° C., and the thus dissolved phase was mixed with water of 80° C. to carry out preliminary emulsification under propeller stirring. After cooling to 25° C., ethanol was added therein, and then, an oil-in-water type emulsion was produced using a high pressure emulsifier (DeBEE 2000, mfd. by B.E.E. International), by passing through the preliminary emulsion 10 times at a shear rate of 10,000,000 s$^{-1}$.

In the table, Comparative Example 4 is a product in which an oil-in-water type emulsion produced in the same manner without using solid fatty material was thickened by adding hydroxyethyl cellulose, and Comparative Example 5 is an aqueous gel produced by simply mixing respective components.

Light transmittance was measured at an absorption wavelength of 550 nm (cell length 1 cm) using an ultraviolet and visible region absorption photometer UV-160 (mfd. by Shimadzu). Viscosity was measured at 25° C. using a B type rotational viscometer (rotor Nos. 1 to 4, rotational speed 6 r/min). Oiliness and moist feeling as the cosmetics were evaluated by a panel of 20 experts, by washing their face with a cleansing foam, applying each cosmetic to the face and then judging the oiliness at the time of application and the moist feeling after drying.

TABLE 4

|  | Inv. Ex. 18 | Comp. Ex. 4 | Comp. Ex. 5 |
|---|---|---|---|
| Sodium N-stearoyl-L-glutamate | 1.0 | 1.0 | — |
| Squalane | 8.0 | 8.0 | — |
| Glycerol | 7.0 | 7.0 | 7.0 |
| Ethanol | 7.0 | 7.0 | 7.0 |
| Cetanol | 3.0 | — | — |
| Stearyl alcohol | 2.0 | — | — |
| Purified water | 72.0 | 76.2 | 85.2 |
| Hydroxyethyl cellulose | — | 0.8 | 0.8 |
| Light transmittance (%) | 73 | 71 | 89 |
| Viscosity (mPa · s) | 23,000 | 21,300 | 24,100 |
| Oiliness | good | good | bad |
| Moist feeling | good | bad | bad |

As shown in Table 4, the oil-in-water type emulsion cosmetic of the invention has excellent transparency, shows high viscosity without using a thickener and is excellent in oiliness and moist feeling.

Inventive Example 19

A 5 kg portion of a mixture consisting of 1.0 part by weight of N-stearoyl-N-methyltaurine sodium, 10.0 parts by weight of dimethyl polysiloxane 2 cs (mfd. by Shin-Etsu Chemical), 8.0 parts by weight of dipropylene glycol, 3.3 parts by weight of palmitic acid, 2.7 parts by weight of stearic acid and 75.0 parts by weight of purified water was subjected to preliminary emulsification, and a high viscosity oil-in-water type emulsion was produced using a high pressure emulsifier (DeBEE 2000) by passing through the emulsion 3 times at a shear rate of 10,000,000 s$^{-1}$. The thus obtained oil-in-water type emulsion had a viscosity of 27,500 mPa·s, a particle size of 0.2 μm and a light transmittance of 71%. Next, this was diluted by adding 15 kg of purified water to obtain a low viscosity liquid cosmetic having a viscosity of 170 mPa·s, an average particle size of 0.2 μm and a light transmittance of 93%. This liquid cosmetic was produced within a short period of 40 minutes as the total process, requiring 30 minutes for the production of high viscosity oil-in-water type emulsion and 10 minutes for the dilution with purified water. A low viscosity liquid cosmetic having the same composition can also be obtained directly by a high pressure emulsification method without employing the dilution method, but in that case, the high pressure emulsion treating amount became 20 kg which was 4 times larger than the dilution method, and the treating period also became 4 times requiring 120 minutes.

Oil-in-water type emulsion cosmetics of the following examples were produced in the same manner as described in Inventive Example 18.

Inventive Example 20

| Composition: | |
| --- | --- |
| Polyoxyethylene (20) cetyl ether | 1.0% |
| Isopropyl palmitate | 3.0 |
| Glycerol | 12.0 |
| Cholesterol | 4.0 |
| Purified water | 80.0 |

The thus produced oil-in-water type emulsion cosmetic showed a light transmittance of 63%, an average particle size of 0.4 μm and a viscosity of 2,000 mPa·s.

Inventive Example 21

| Composition: | |
| --- | --- |
| N-Stearoyl-L-glutamic acid monosodium | 0.7% |
| Dicapric acid neopentyl glycol | 4.0 |
| Sorbitol | 7.0 |
| Ethanol | 7.0 |
| Cetanol | 3.0 |
| Stearyl alcohol | 2.0 |
| Purified water | 76.3 |

The thus produced oil-in-water type emulsion cosmetic showed a light transmittance of 69%, an average particle size of 0.22 μm and a viscosity of 20,000 mPa·s.

Inventive Example 22

| Composition: | |
| --- | --- |
| Sodium monostearylphosphate | 1.0% |
| Squalane | 7.0 |
| 1,3-Butanediol | 2.2 |
| 12-Hydroxystearic acid | 1.2 |
| Palmitic acid | 1.1 |
| Stearic acid | 0.9 |
| Purified water | 86.6 |

The thus produced oil-in-water type emulsion cosmetic showed a light transmittance of 77%, an average particle size of 0.14 μm and a viscosity of 4,125 mPa·s.

Inventive Example 23

| Composition: | |
| --- | --- |
| N-Stearoyl-L-glutamic acid monosodium | 1.0% |
| Perfluoro polyether | 8.0 |
| Glycerol | 9.4 |
| Ethanol | 4.0 |
| Docosahexaenoic acid | 1.2 |
| Cholesterol | 2.3 |
| Purified water | 74.1 |

The thus produced oil-in-water type emulsion cosmetic showed a light transmittance of 83%, an average particle size of 0.08 μm and a viscosity of 13,000 mPa·s.

Inventive Example 24

| Composition: | |
| --- | --- |
| N-Stearoyl-N-methyltaurine sodium | 2.0% |
| Dimethyl polysiloxane (6 cs) | 7.0 |
| Cetanol | 4.8 |
| Stearyl alcohol | 3.2 |
| Glycerol | 5.5 |
| Purified water | 77.5 |

The thus produced oil-in-water type emulsion cosmetic showed a light transmittance of 60%, an average particle size of 0.43 μm and a viscosity of 4,200 mPa·s.

Inventive Example 25

| Composition: | |
| --- | --- |
| Stearyltrimethylammonium chloride | 2.0% |
| Dimethyl polysiloxane (2 cs) | 20.0 |
| Dipropylene glycol | 15.0 |
| Palmitic acid | 2.4 |
| Stearic acid | 3.6 |
| Ceramide-analogous substance* | 5.0 |
| Purified water | 52.0 |

*N-(2-hydroxy-3-hexadecyloxypropyl)-N-2-hydroxyethylhexadecanamide

The thus produced oil-in-water type emulsion cosmetic showed a light transmittance of 75%, an average particle size of 0.1 μm and a viscosity of 27,000 mPa·s.

Inventive Example 26

| Composition: | |
| --- | --- |
| N-Stearoyl-L-glutamic acid monosodium | 0.6% |
| Squalane | 3.0 |
| Cholesterol | 0.2 |
| Sorbitol | 4.0 |
| Ethanol | 7.0 |
| Phytosphingosine | 3.0 |
| Palmitic acid | 1.2 |

-continued

| Composition: | |
|---|---|
| Stearic acid | 1.8 |
| Purified water | 79.2 |

The thus produced oil-in-water type emulsion cosmetic showed a light transmittance of 70%, an average particle size of 0.18 μm and a viscosity of 18,900 mPa·s.

The oil-in-water type emulsion cosmetics of Inventive Examples 20 to 26 were stable even after one year of storage at a temperature of from −5 to 40° C.

The entire disclosure of each and every foreign patent application from which the benefit of foreign priority has been claimed in the present application is incorporated herein by reference, as if fully set forth.

What is claimed is:

1. An oil-in-water emulsion comprising:
    (A) at least one hydrophilic surface active agent selected from the group consisting of:
        polyoxyethylene(4) lauryl ether phosphate sodium salt,
        polyoxyetheylene(6) tridecyl ether acetate sodium salt, and
        polyoxyethylene(30) cetyl ether;
    (B) one or more oily component(s) and
    (C) a water phase;
    wherein said oil-in-water emulsion has an average particle size ranging from 0.01 to 0.2 μm and a light transmittance at 550 nm of 50% or more,
    wherein the weight ratio of component (B) is from 11 to 38 based on 1 of the component (A).

2. The oil-in-water emulsion of claim 1, wherein the emulsion contains 0.1 to 6% by weight of the hydrophilic surface active agent (A).

3. The oil-in-water emulsion of claim 1, wherein said hydrophilic surface active agent (A) is polyoxvethylene(4) lauryl ether phosphate sodium salt.

4. The oil-in-water emulsion of claim 1, wherein said hydrophilic surface active agent is polyoxyetheylene(6) tridecyl ether acetate sodium salt.

5. The oil-in-water emulsion of claim 1, wherein said hydrophilic surface active agent is polyoxyethylene(30) cetyl ether.

6. The oil-in-water emulsion of claim 1, wherein the emulsion contains 1 to 70% by weight of the at least one oily component (B).

7. The oil-in-water emulsion of claim 1, wherein the emulsion contains 1 to 70% by weight of the at least one oily component (B) selected from the group consisting of liquid paraffin, squalane, neopentyl glycol dicaprate, ethylene glycol monolauryl ether, perfluoro polyether and dimethyl polysiloxane.

8. The oil-in-water emulsion of claim 1, wherein said water phase (C) comprises 10 to 98.9% by weight of the oil-in-water emulsion.

9. The oil-in-water emulsion of claim 1, wherein said oil-in-water emulsion contains 1-33% by weight of at least one water-soluble alcohol.

10. The oil-in-water emulsion of claim 1, wherein said oil-in-water emulsion contains 1-33% by weight of at least one water-soluble alcohol selected from the group consisting of methyl alcohol, ethyl alcohol, propyl alcohol, isopropyl alcohol, ethylene glycol, propylene glycol, 1,3-butylene glycol, glycerol, sorbitol, mannitol, diethylene glycol, dipropylene glycol, polyethylene glycol having a molecular weight ranging from 400 to 20,000), sorbitan, sorbitol, maltose, maltotriose and sodium hyaluronate.

11. The oil-in-water emulsion according to claim 1, further comprising a fatty component which is solid at 25° C. in an amount of 2 to 20% by weight of said emulsion and at a ratio range from 0.01 to 0.5 part solid fatty component per 1 part liquid oily component (B);
    wherein said emulsion has a viscosity ranging from 200 to 1,000,000 mPa·s at 25° C.

12. The oil-in-water emulsion of claim 11, wherein said solid fatty component is a saturated aliphatic alcohol having 12 to 24 carbon atoms or a saturated fatty acid having from 12 to 24 carbon atoms.

13. The oil-in-water emulsion according to claim 1, wherein said emulsion is obtained by applying a shear force corresponding to a shear rate of 1,000,000 $s^{-1}$ or more to a mixture of component (A), component (B) and component (C).

14. The oil-in-water emulsion of claim 1 that is produced using a high-pressure commercial emulsifier that applies a shear force corresponding to a shear rate of 10,000 $s^{-1}$ or more.

15. A cosmetic comprising the oil-in-water emulsion according to claim 1.

16. The cosmetic of claim 15 selected from the group consisting of a hair cosmetic, shaving cosmetic, and skin cosmetic.

17. The cosmetic of claim 15, further comprising a water-soluble high polymer.

18. A method for making an oil-in-water emulsion comprising:
    applying a shear force corresponding to a shear rate of 10,000 $s^{-1}$ or more to a mixture of component (A), component (B) and component (C) for a time and under conditions suitable for forming an emulsion having an average particle size ranging from 0.01 to 0.2 μm, wherein the weight ratio of component (B) is from 11 to 38 based on 1 of the component (A);
    wherein (A), (B) and (C) are:
    (A) a hydrophilic surface active agent, having a dynamic surface tension of 57 mN/m or less (A) and comprises at least one hydrophilic surface active agent selected from the group consisting of:
    polyoxyethylene(4) lauryl ether phosphate sodium salt,
    polyoxyetheylene(6) tridecyl ether acetate sodium salt, and
    polyoxyethylene(30) cetyl ether,
    (B) an oily component, and
    (C) a water phase.

* * * * *